United States Patent
McLuen et al.

(10) Patent No.: US 6,811,755 B2
(45) Date of Patent: Nov. 2, 2004

(54) MULTI-WELL ROTARY SYNTHESIZER

(75) Inventors: Gary R. McLuen, Alameda, CA (US); Richard J. Hanney, Alameda, CA (US); Daniel W. Hugens, Alamo, CA (US)

(73) Assignee: McLuen Design, Inc., Port Townsend, WA (US)

(*) Notice: Subject to any disclaimer, the term of this patent is extended or adjusted under 35 U.S.C. 154(b) by 487 days.

(21) Appl. No.: 09/901,949

(22) Filed: Jul. 9, 2001

(65) Prior Publication Data

US 2001/0051114 A1 Dec. 13, 2001

Related U.S. Application Data

(63) Continuation of application No. 09/097,966, filed on Jun. 16, 1998, now Pat. No. 6,270,730.

(51) Int. Cl.⁷ ............................................. C08F 283/00
(52) U.S. Cl. ............................ 422/131; 422/62; 422/81
(58) Field of Search .................................. 422/131, 134, 422/188, 189, 63–65, 81, 99, 101, 102, 104, 129, 130; 935/87, 88

(56) References Cited

U.S. PATENT DOCUMENTS

| | | | |
|---|---|---|---|
| 2,684,255 A | * 7/1954 | Abele et al. ................. | 285/229 |
| 3,215,500 A | 11/1965 | Bittner | |
| 3,538,950 A | 11/1970 | Porteners ..................... | 137/608 |
| 3,583,230 A | 6/1971 | Patterson ..................... | 73/422 |
| 3,838,013 A | 9/1974 | Bergeron ..................... | 195/139 |
| 3,844,306 A | * 10/1974 | Hill ............................ | 137/256 |
| 3,917,455 A | 11/1975 | Bak ......................... | 23/253 R |
| 4,353,989 A | * 10/1982 | Bender et al. ............... | 422/131 |
| 4,360,360 A | * 11/1982 | Chiknas ........................ | 436/45 |
| 4,415,732 A | 11/1983 | Caruthers et al. ............. | 536/27 |
| 4,458,066 A | 7/1984 | Caruthers et al. ............. | 536/27 |

(List continued on next page.)

FOREIGN PATENT DOCUMENTS

| | | | |
|---|---|---|---|
| AU | 14149/76 | 11/1977 | ............. F16L/1/14 |
| DE | 39 08725 A01 | 9/1990 | .......... G01N/35/00 |
| DE | 196 42 777 A1 | 5/1998 | ............ B01J/19/00 |
| DE | 297 19 919 U1 | 5/1999 | ............ B01J/19/00 |
| FR | 1143849 | 10/1957 | |

(List continued on next page.)

OTHER PUBLICATIONS

L.E. Sindelar and J.M. Jaklevic, "High–Throughout DNA Synthesis in a Multichannel Format," Nucleic Acids Research, 1995, vol. 23, No. 6, pp. 982–987, Oxford University Press.

(List continued on next page.)

Primary Examiner—Kiley Stoner
(74) Attorney, Agent, or Firm—Haverstock & Owens LLP

(57) ABSTRACT

An apparatus for synthesizing polymer chains includes a controller, a plurality of precision fit vials circularly arranged in multiple banks on a cartridge, a drain corresponding to each bank of vials, a chamber bowl, a plurality of valves for delivering reagents to selective vials, and a waste tube system for purging material from the vials. A purging operation can be selectively performed on one or more of the banks of vials. The multiple banks of valves provide an additional number of reagent choices while operating in a serial mode and faster reagent distribution while operating in a parallel mode. The plurality of vials are stored in the cartridge and are divided among individual banks wherein each bank of vials has a corresponding drain. There is at least one waste tube system for expelling the reagent solution from vials within a particular bank of vials when the waste tube system is coupled to the corresponding drain. The cartridge holding the plurality of vials rotates relative to the stationary banks of valves and the waste tube system. The controller rotates the cartridge and operates the banks of valves and the waste tube system in response to the required sequence of dispensing various reagent solutions and flushing appropriate vials in order to form the desired polymer chain within each vial.

27 Claims, 8 Drawing Sheets

U.S. PATENT DOCUMENTS

| | | | | |
|---|---|---|---|---|
| 4,748,859 A | | 6/1988 | Magnussen, Jr. et al. | 73/864.01 |
| 4,810,471 A | | 3/1989 | Wachob et al. | 422/103 |
| 4,816,513 A | | 3/1989 | Bridgham et al. | 525/54.11 |
| 4,837,159 A | | 6/1989 | Yamada | 436/45 |
| 4,849,648 A | * | 7/1989 | Longardner | 290/54 |
| 4,874,691 A | | 10/1989 | Chandler | 435/7 |
| 5,047,524 A | | 9/1991 | Andrus et al. | 536/27 |
| 5,053,454 A | * | 10/1991 | Judd | 525/54.11 |
| 5,066,600 A | * | 11/1991 | Antonevich et al. | 436/52 |
| 5,093,268 A | | 3/1992 | Leventis et al. | 436/172 |
| 5,096,807 A | | 3/1992 | Leaback | 435/6 |
| 5,112,736 A | | 5/1992 | Caldwell et al. | 435/6 |
| 5,132,418 A | | 7/1992 | Caruthers et al. | 536/27 |
| 5,171,537 A | | 12/1992 | Wainwright et al. | 422/100 |
| 5,239,484 A | | 8/1993 | Hayashi et al. | 364/500 |
| 5,262,530 A | | 11/1993 | Andrus et al. | 536/25.31 |
| 5,273,718 A | | 12/1993 | Skold et al. | 422/101 |
| 5,297,288 A | | 3/1994 | Hemminger et al. | 395/700 |
| 5,324,483 A | | 6/1994 | Cody et al. | 422/131 |
| 5,344,613 A | | 9/1994 | Nokihara et al. | 422/131 |
| 5,356,776 A | | 10/1994 | Kambara et al. | 435/6 |
| 5,368,823 A | | 11/1994 | McGraw et al. | 422/134 |
| 5,380,495 A | | 1/1995 | Chang et al. | 422/131 |
| 5,395,594 A | | 3/1995 | Nokihara et al. | 422/135 |
| 5,424,038 A | * | 6/1995 | Benz et al. | 422/100 |
| 5,427,930 A | | 6/1995 | Birkenmeyer et al. | 435/91.52 |
| 5,437,979 A | | 8/1995 | Rampal et al. | 435/6 |
| 5,453,247 A | | 9/1995 | Beavis et al. | 422/68.1 |
| 5,468,606 A | | 11/1995 | Bogart et al. | 435/5 |
| 5,472,672 A | * | 12/1995 | Brennan | 422/131 |
| 5,496,523 A | | 3/1996 | Gazit et al. | 422/100 |
| 5,503,805 A | | 4/1996 | Sugarman et al. | 422/131 |
| 5,510,270 A | | 4/1996 | Fodor et al. | 436/518 |
| 5,522,272 A | | 6/1996 | Vecere et al. | 73/864.62 |
| 5,529,756 A | | 6/1996 | Brennan | 422/131 |
| 5,541,113 A | | 7/1996 | Siddigi et al. | 436/56 |
| 5,545,531 A | | 8/1996 | Rava et al. | 435/6 |
| 5,547,839 A | | 8/1996 | Dower et al. | 435/6 |
| 5,556,598 A | | 9/1996 | Raybuck et al. | 422/10 D |
| 5,563,033 A | | 10/1996 | Lawrence et al. | 435/6 |
| 5,571,639 A | | 11/1996 | Hubbell et al. | 430/7 |
| 5,575,914 A | | 11/1996 | Jeyendran | 210/445 |
| 5,593,839 A | | 1/1997 | Hubbell et al. | 435/6 |
| 5,597,694 A | | 1/1997 | Munroe et al. | 435/6 |
| 5,605,662 A | | 2/1997 | Heller et al. | 422/68.1 |
| 5,632,957 A | | 5/1997 | Heller et al. | 422/68.1 |
| 5,633,365 A | | 5/1997 | Stokke et al. | 536/24.31 |
| 5,639,428 A | | 6/1997 | Cottingham | 422/112 |
| 5,645,114 A | | 7/1997 | Bogen et al. | 141/145 |
| 5,645,801 A | | 7/1997 | Bouma et al. | 422/68.1 |
| 5,648,266 A | * | 7/1997 | Astle | 435/308.1 |
| 5,653,939 A | | 8/1997 | Hollis et al. | 422/50 |
| 5,690,894 A | | 11/1997 | Pinkel et al. | 422/68.1 |
| 5,707,797 A | | 1/1998 | Windle | 435/6 |
| 5,720,923 A | | 2/1998 | Haff et al. | 422/68.1 |
| 5,720,928 A | | 2/1998 | Schwartz | 422/186 |
| 5,736,333 A | | 4/1998 | Livak et al. | 435/6 |
| 5,744,305 A | | 4/1998 | Fodor et al. | 435/6 |
| 5,762,881 A | | 6/1998 | Harness et al. | 422/132 |
| 5,807,523 A | * | 9/1998 | Watts et al. | 422/64 |
| 5,851,491 A | | 12/1998 | Moulton | 422/101 |
| 5,855,852 A | | 1/1999 | Bienhaus et al. | 422/102 |
| 5,861,094 A | | 1/1999 | Goehde | 210/232 |
| 5,976,470 A | * | 11/1999 | Maiefski et al. | 422/103 |
| 6,048,457 A | | 4/2000 | Kopaciewicz et al. | 210/321.6 |
| 6,083,682 A | * | 7/2000 | Campbell et al. | 435/4 |
| 6,123,905 A | | 9/2000 | Torti et al. | 422/100 |
| 6,264,891 B1 | * | 7/2001 | Heyneker et al. | 422/64 |
| 6,270,730 B1 | * | 8/2001 | McLuen et al. | 422/131 |
| 6,319,236 B1 | | 11/2001 | Bock | 604/240 |
| 6,566,145 B2 | | 5/2003 | Brewer | 436/178 |
| 2001/0000723 A1 | * | 5/2001 | McLuen et al. | 422/100 |
| 2001/0001035 A1 | * | 5/2001 | McLuen et al. | 422/100 |
| 2001/0007644 A1 | * | 7/2001 | McLuen et al. | 422/131 |
| 2001/0051114 A1 | * | 12/2001 | McLuen et al. | 422/131 |

FOREIGN PATENT DOCUMENTS

| | | | |
|---|---|---|---|
| GB | 2 146 030 A | 4/1985 | C07H/1/00 |
| WO | WO 91/13084 | 9/1991 | C07K/1/04 |
| WO | WO 97/26540 | 7/1997 | G01N/35/00 |
| WO | WO 98/10857 | 3/1998 | B01J/19/00 |
| WO | WO 98/36829 | 8/1998 | B01J/19/00 |
| WO | WO 98/39099 | 9/1998 | B01J/3/00 |
| WO | WO 98/57181 | 12/1998 | G01N/35/10 |
| WO | WO 99/65602 | 12/1999 | B01J/19/00 |

OTHER PUBLICATIONS

Robert L. Letsinger and V. Mahadevan, "Stepwise Synthesis of Oligodeoxyribonucleotides on an Insoluble Polymer Support," JAm Chem Soc, vol. 88:22, pp. 5319–5324, Nov. 20, 1966.

VICI "Injectors and Switching Valves" Valco Instruments Co, Inc. Valco International, Dec. 12, 1999, p. 1–2.

Valve Handbook by Philip L. Skousen, McGraw–Hill, 1997, pp. 58–60.

* cited by examiner

MULTI-WELL ROTARY SYNTHESIZER

RELATED APPLICATIONS

This Patent application is a continuation of co-pending U.S. patent application Ser. No. 09/097,966, filed on Jun. 16 1998 now U.S. pat. no. 6,270,730 and entitled MULTI-WELL ROTARY SYNTHESIZER.

FIELD OF THE INVENTION

The present invention relates to the field of synthesizers. More particularly, this invention relates to synthesizers that utilize multiple banks of vials to synthesize custom sequence defined oligonucleotides, polymers, and other organic compounds.

BACKGROUND OF THE INVENTION

Oligonucleotides are playing an increasingly important role in diagnostic medicine, forensic medicine, and molecular biology research. In addition to oligonucleotides, polymers such as peptides, polynucleotides, and other organic chains are also very important in scientific research.

Accordingly, the use of and demand for synthetic oligonucleotides, polymers, and organic chains has increased. In turn, this has spawned development of new synthesis systems and methods for basic procedures for custom sequence defined oligonucleotides, polymers, and other organic chains.

Typically, the present automated systems and methods place a solid support such as controlled pore glass beads (CPG) into a plurality of individual vials which provide a stable anchor to initiate the synthesis process. Using a series of valves, the selected reagents are sequentially placed into the appropriate vial in a predetermined sequence. Contact of the reagent with the CPG inside each of the vials causes a reaction that results in sequenced growth thereon. Sequential deposits of the selected reagents within the vials build the predetermined sequence.

A flushing procedure is typically utilized after a particular reagent is placed into one of the vials for a predetermined amount of time. While the particular reagent contacts the CPG a reaction produces a sequenced growth on the CPG. In conventional synthesis machines the flushing procedure is performed on all the vials simultaneously. During a flushing operation within conventional synthesis machines, all the reagents within the plurality of individual vials are flushed and expelled through a shared central orifice within the synthesis machine. After completion of a flushing operation, the plurality of vials are then capable of receiving another reagent.

In *High Throughput DNA Synthesis in a MultiChannel Format*, L. E. Sindelar and J. M. Jaklevic teach an approach to high throughput parallel DNA synthesis in which a multi-vial format is utilized. The reactions are carried out in open vials. Each vial contains CPG to form the substrate for the synthesis and a high density filter bottom to retain the CPG within each vial. There is a common vacuum line that is coupled to all the vials. This common vacuum line simultaneously flushes the material contained within all the vials. The synthesis of a DNA sequence is carried out by directly dispensing reagents into individual reaction vials. A computer controls the sequence in which reagents are dispensed and timing periodic flushing operations to expel material from the reaction vials.

U.S. Pat. No. 5,529,756, by Brennan, teaches an apparatus and method for polymer synthesis utilizing arrays. This apparatus includes an array of nozzles with each nozzle coupled to a reservoir containing a reagent and a base assembly having an array of reaction vials. A transport mechanism aligns the reaction vials and selected nozzles to deposit an appropriate reagent to a selected vial. Each of the reaction vials has an inlet for receiving a reagent and an outlet for expelling a material. To perform a flushing operation, this apparatus creates a pressure differential between the inlet and outlet of the array of vials. During the flushing operation, material within each of the array of vials are simultaneously expelled.

A retaining device is customarily utilized to ensure that the CPG remains within the corresponding vial during the flushing procedure. This retaining device is located within each individual vial and is positioned to prevent the CPG from exiting the orifice during the flushing procedure.

Conventional automated synthesis systems perform the flushing operation simultaneously on all vials within the system. Conventional automated synthesis systems lack the ability to selectively perform the flushing operation on groups of vials within the system.

What is needed is a synthesizer that is configured to selectively perform depositing and flushing operations on groups of vials within the system.

SUMMARY OF THE INVENTION

A multi-well rotary synthesizer includes a controller, a plurality of precision fit vials circularly arranged in multiple banks on a cartridge, a drain corresponding to each bank of vials, a chamber bowl, a plurality of valves for delivering reagents to selective vials, and a waste tube system for purging material from the vials. The banks of vials can be selectively purged, allowing the banks of vials to be used to synthesize different polymer chains. Further, the multiple banks of valves provide an additional number of reagent choices while operating in a serial mode and faster reagent distribution while operating in a parallel mode.

The plurality of vials are held within the cartridge and are divided among individual banks. Preferably, each individual bank of vials has a corresponding drain. There is at least one waste tube system for expelling the reagent solution from vials within a particular bank of vials when the waste tube system is coupled to the corresponding drain. The cartridge holding the plurality of vials rotates relative to the stationary banks of valves and the waste tube system. The controller controls a motor to rotate the cartridge. The controller also operates the banks of valves and the waste tube system in response to the required sequence of dispensing various reagent solutions and flushing appropriate vials in order to create the desired polymer chain.

A frit is inserted into each vial and serves as a filter and to hold the CPG within the vial. The interior of each vial is precision bored to ensure a tight consistent seal with the corresponding frit. This consistent seal with the frit for every vial also results in a consistent reagent solution flow through every vial. The exterior of each vial also has a precise dimension to consistently fit within the cartridge and provide a pressure tight seal around each vial within the cartridge.

DETAILED DESCRIPTION OF THE PRESENT INVENTION

Figure 1:
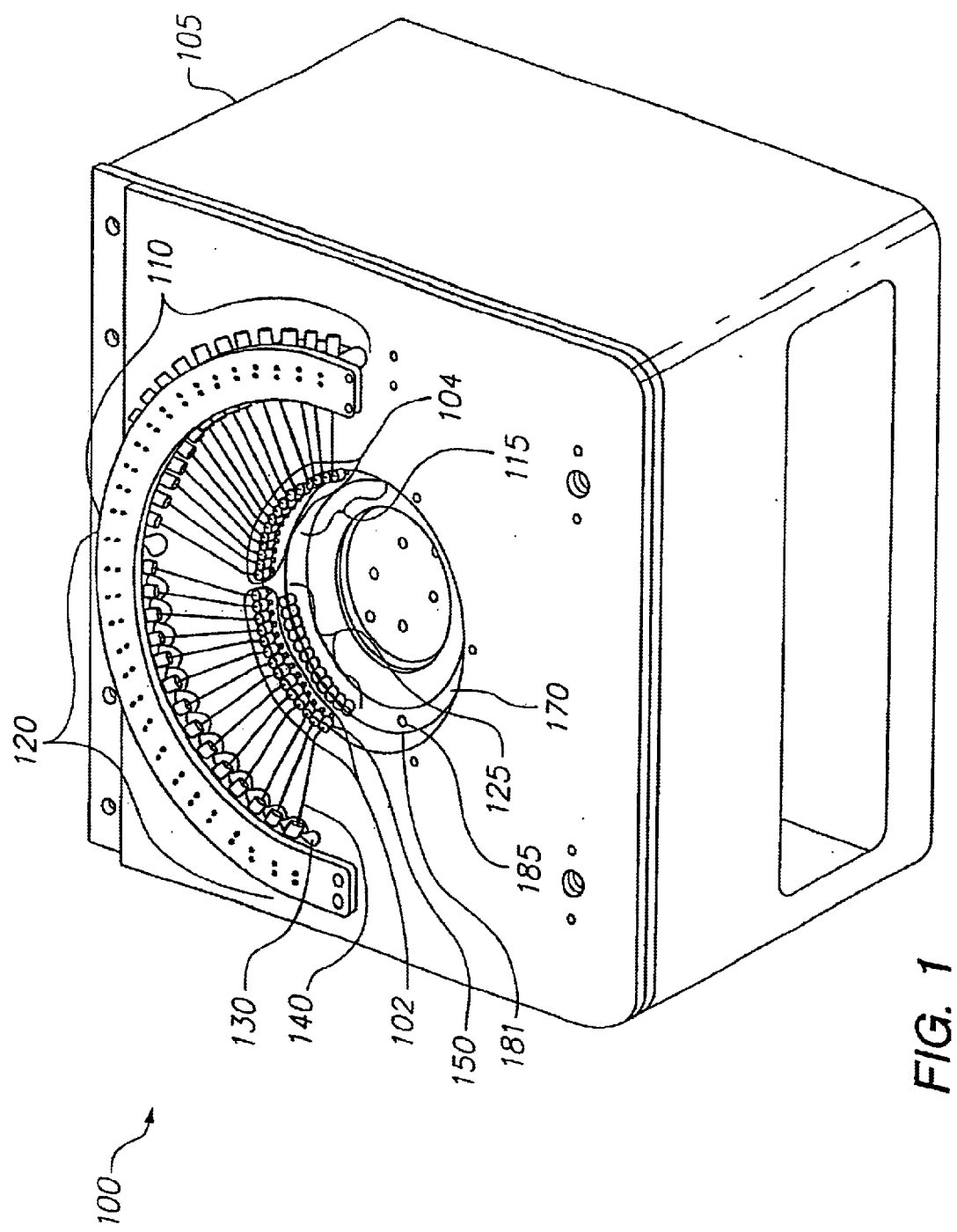
FIG. 1 illustrates a perspective view of the synthesizer of the present invention.

While the present invention will be described with reference to several specific embodiments, the description is illustrative of the present invention and is not to be construed as limiting the invention. Various modifications to the present invention can be made without departing from the scope and spirit of the present invention. For the sake of clarity and a better understanding of the present invention, common components share common reference numerals throughout various figures.

FIG. 1 illustrates a synthesizer 100. The synthesizer 100 is designed for building a polymer chain by sequentially adding polymer units to a solid support in a reagent solution. The solid support generally resides within a vial and various reagent solutions are sequentially added to the vial. Before an additional reagent solution is added to the vial, the previous reagent solution is preferably purged from the vial. Although, the synthesizer 100 is particularly suited for building sequence defined oligonucleotides, the synthesizer 100 is also configured to build any other desired polymer chain or organic compound. The term "polymer chain" is defined as a unit that is bound to other units of the same or different kind to form a polymer chain, such as oligonucleotides and peptide chains. It is important to note that although the present invention is described in context of specific applications, the present invention should not be limited to these specific examples disclosed herein.

The synthesizer 100 preferably comprises at least a bank of valves and at least one bank of vials. Within each bank of vials, there is at least one vial for holding the solid support and for containing a reagent solution such that a polymer chain can be synthesized. Within the bank of valves, there are preferably a plurality of valves configured for selectively dispensing a reagent solution into one of the vials. The synthesizer 100 is preferably configured to allow each bank of vials to be selectively purged of the presently held reagent solution. Additional banks of valves provide the synthesizer 100 with greater flexibility. For example, each bank of valves can be configured to distribute reagent solutions to a particular bank of vials in a parallel fashion to minimize the processing time. Alternatively, multiple banks of valves can be configured to distribute reagent solutions to a particular bank of vials in series thus allowing the synthesizer 100 to hold a larger number of different reagent solutions, thus being able to create complex polymer chains.

FIG. 1 illustrates an exterior perspective view of a rotary synthesizer 100. As illustrated in FIG. 1, the synthesizer 100 includes a base 105, a cartridge 170, a first bank of vials 115, a second bank of vials 125, a plurality of dispense lines 140, a plurality of fittings 150, a first bank of valves 110 and a second bank of valves 120. Within each of the banks of valves 110 and 120, there is preferably at least one valve.

Within each of the banks of vials 115 and 125, there is preferably at least one vial. Each of the valves is capable of selectively dispensing a reagent solution into one of the vials. As stated before, each of the vials is preferably configured for retaining a solid support such as CPG and holding a reagent solution. Further, as each reagent solution is sequentially deposited within the vial and sequentially purged therefrom, a polymer chain is generated.

Preferably, there is a plurality of reservoirs (not shown) each containing a specific reagent solution to be dispensed to one of the plurality of valves 130. Each of the valves within the first bank and second bank of valves 110 and 120, is coupled to a corresponding reservoir. Each of the plurality of reservoirs is pressurized. As a result, as each valve is opened, a particular reagent solution from the corresponding reservoir is dispensed to a corresponding vial.

Each of the plurality of dispense lines 140 is coupled to a corresponding one of the valves within the first and second banks of valves 110 and 120. Each of the plurality of dispense lines 140 provides a conduit for transferring a reagent solution from the valve to a corresponding vial. Each one of the plurality of dispense lines 140 is preferably configured to be flexible and semi-resilient in nature. Preferably, the plurality of dispense lines 140 are each coated with Teflon® which is more resistant to deterioration upon contact with reagent solutions and provides an adequate seal between the plurality of valves 130 and the plurality of fittings 150. Further, each of the plurality of fittings 150 is preferably coupled to one of the plurality of dispense lines 140. The plurality of fittings 150 are preferably configured to prevent the reagent solution from splashing outside the vial as the reagent solution is dispensed from a cap to a particular vial positioned below the cap.

As shown in FIG. 1, the first and second banks of valves 110 and 120 each have thirteen valves. In FIG. 1, the number of valves in each bank is merely for exemplary purposes. It is preferable to have fifteen valves for each bank even though the illustrated cartridge 170 only has twelve vials per bank. The present invention provides greater flexibility in creating complex polymer chains by including a greater number of valves than vials per bank. It should be apparent to those skilled in the art that any appropriate number of valves can be included within each bank of valves.

Each of the vials within the first bank of vials 115 and the second bank of vials 125 is presently shown resting in one of a plurality of receiving holes 185 within the cartridge 170. Preferably, each of the vials within the corresponding plurality of receiving holes 185 is positioned in a substantially vertical orientation. Each of the vials is configured to retain a solid support such as CPG and hold a reagent solution. Preferably CPG is utilized as this solid support. Alternatively, any other appropriate solid support can be used to support the polymer chain being synthesized.

In use, each of the valves selectively dispenses a reagent solution through one of the plurality of dispense lines 140 and fittings 150. The first and second banks of valves 110 and 120 are preferably coupled to the base 105 of the synthesizer 100. The cartridge 170 which contains the plurality of vials 181 rotates relative to the synthesizer 100 and relative to the first and second banks of valves 110 and 120. By rotating the cartridge 170, a particular vial 181 can be positioned under a specific valve such that the corresponding reagent solution from this specific valve is dispensed into this vial. Further, the first and second banks of valves 110 and 120 are capable of simultaneously and independently dispensing reagent solutions into corresponding vials.

Figure 2:
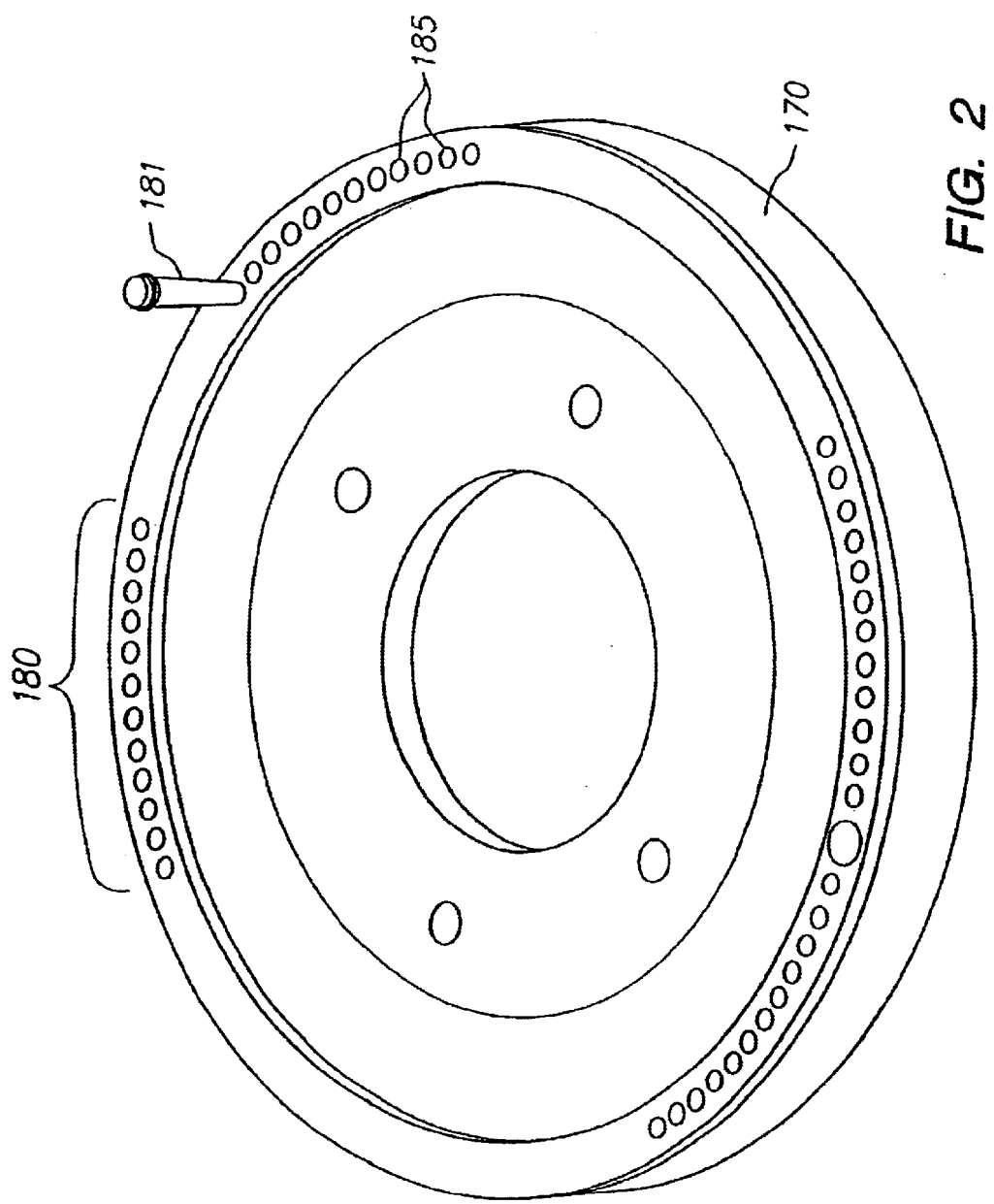
FIG. 2 illustrates the preferred cartridge of the present invention.

FIG. 2 illustrates a detailed view of the cartridge 170. Preferably, the cartridge 170 is circular in shape such that the cartridge 170 is capable of rotating in a circular path relative to the base 105 and the first and second banks of valves 110 and 120. The cartridge 170 has a plurality of receiving holes 185 on its upper surface around the peripheral edge of the cartridge 170. Each of the plurality of receiving holes 185 is configured to hold one of the vials 181 within the first bank of vials 115 and the second bank of vials 125. The plurality of receiving holes 185 as shown on the cartridge 170 are divided up among four banks. A bank 180 illustrates one of the four banks on the cartridge 170 and contains twelve receiving holes wherein each receiving hole is configured to hold a vial. An exemplary vial 181 is shown being inserted into one of the plurality of receiving holes 185. The total number of receiving holes shown on the cartridge 170 includes forty-eight (48) receiving holes divided into four banks of twelve receiving holes each. The number of receiving holes and the configuration of the banks of receiving holes is shown on the cartridge 170 for exemplary purposes only. It should be apparent to those skilled in the art that any appropriate number of receiving holes and banks of receiving holes can be included in the cartridge 170. Preferably, the receiving holes 185 within the cartridge each have a precise diameter for accepting the vials 181, which also each have a corresponding precise exterior dimension to provide a pressure-tight seal when the vials 181 are inserted into the receiving holes 185.

Figure 3:
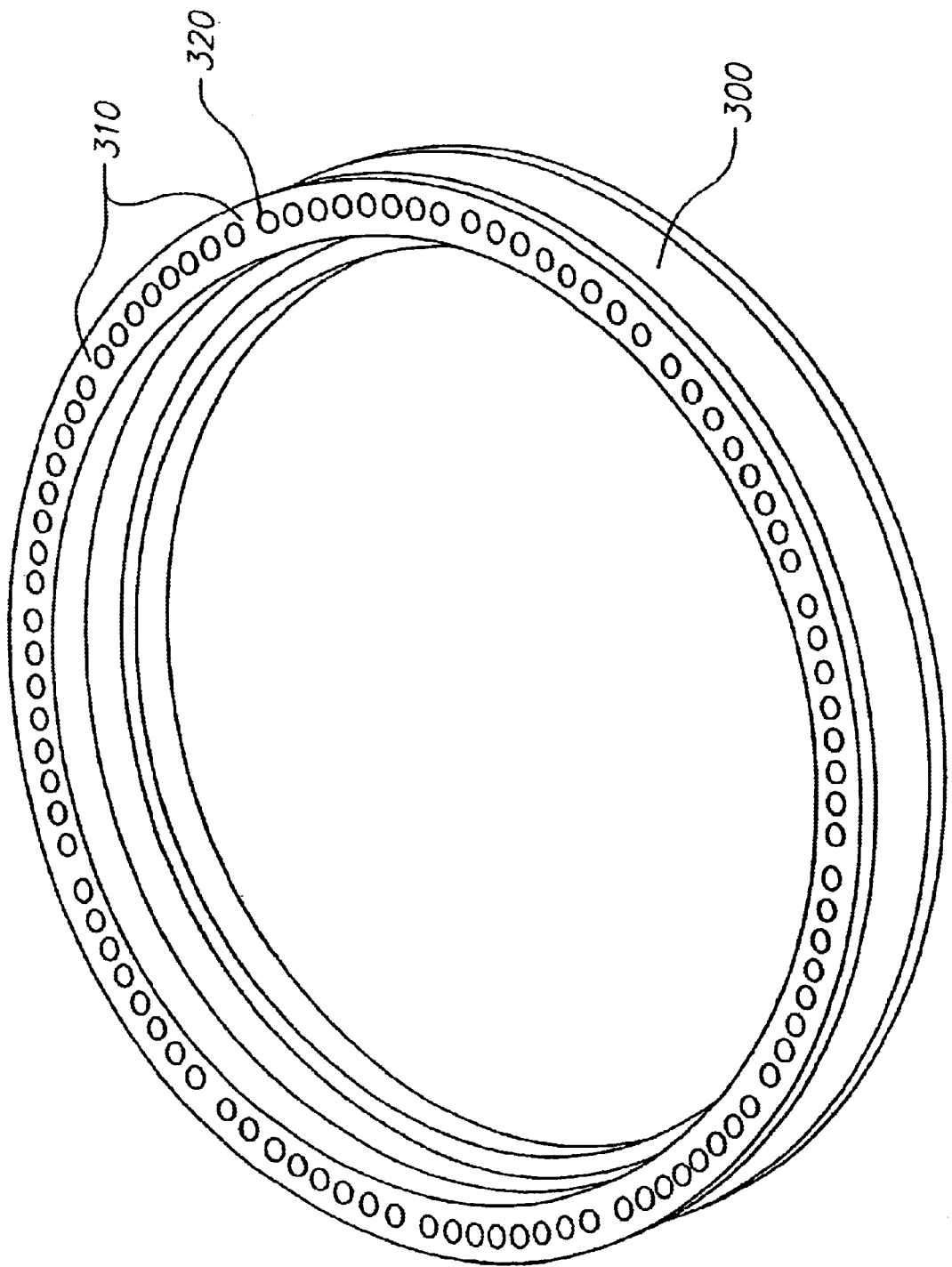
FIG. 3 illustrates a perspective view of an alternate cartridge."

FIG. 3 illustrates an alternative cartridge 300. The cartridge 300 is similar to the cartridge 170 shown in FIGS. 1 and 2. Each of the receiving holes 320 is configured to hold a vial 181. A plurality of receiving holes are grouped together to form a bank of receiving holes 310. The cartridge 300 contains a total of ninety-six (96) receiving holes grouped into twelve banks, each bank including eight receiving holes. The number of receiving holes and the configuration of the banks of receiving holes included on the cartridge 300 is exemplary only.

Figure 4:
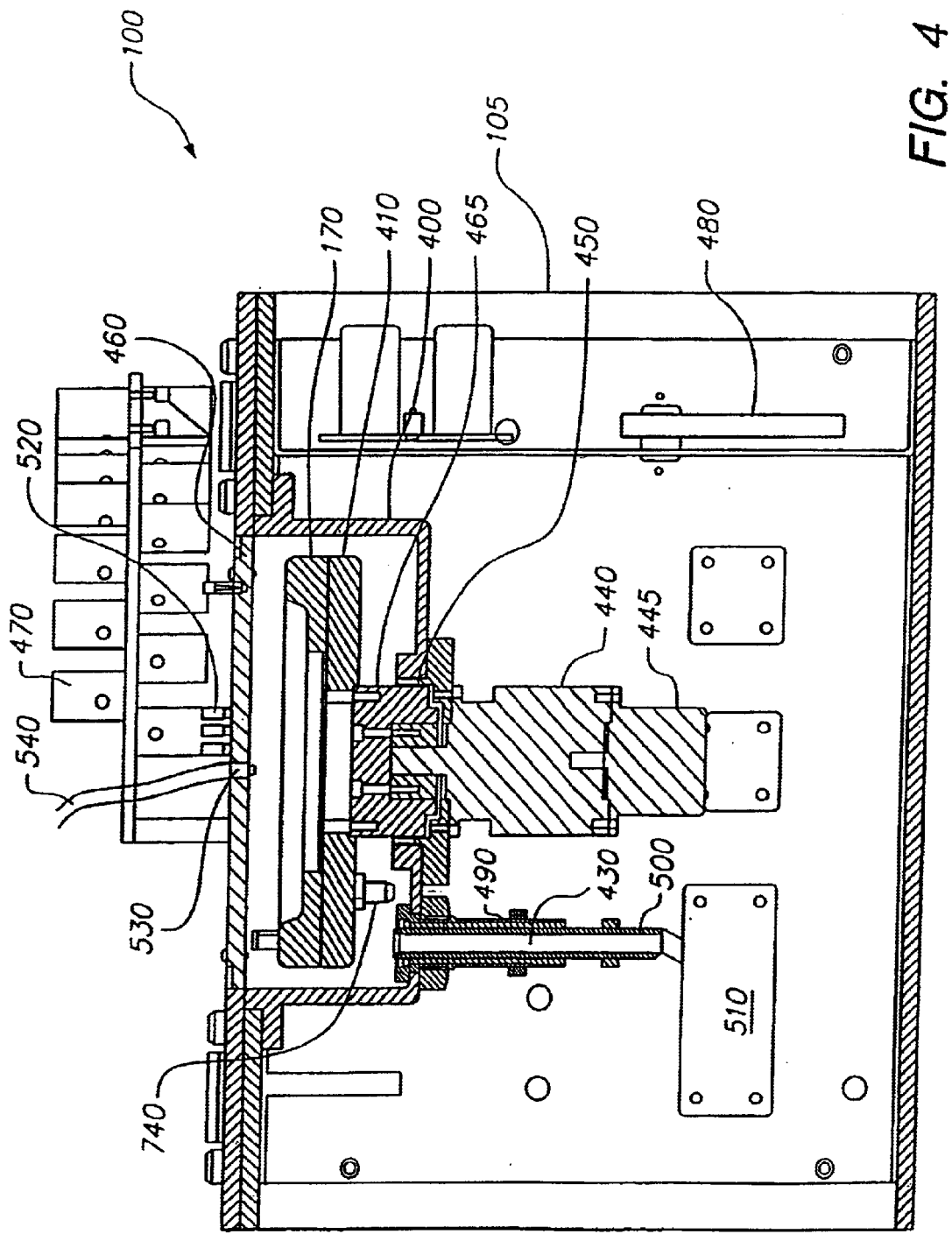
FIG. 4 illustrates a cross-sectional view of the synthesizer of the present invention.

FIG. 4 illustrates a cross sectional view of the synthesizer 100. As illustrated in FIG. 4, the synthesizer 100 includes the base 105, a set of valves 470, a motor 445, a gear box 440, a chamber bowl 400, a drain plate 410, a drain 740, the cartridge 170, a chamber seal 450, a motor connector 465, a waste tube system 430, a controller 480, and a clear window 460. The valves 470 are coupled to the base 105 of the synthesizer 100 and are preferably positioned above the cartridge 170 around the outside edge of the base 105. This set of valves 470 preferably contains fifteen individual valves which each deliver a corresponding reagent solution in a specified quantity to a vial held in the cartridge 170 positioned below the valve. Each of the valves may dispense the same or different reagent solutions depending on the user-selected configuration. When more than one valve dispenses the same reagent solution, the set of valves 470 is capable of simultaneously dispensing a reagent solution to multiple vials within the cartridge 170. When the valves 470 each contain different reagent solutions, each one of the valves 470 is capable of dispensing a corresponding reagent solution to any one of the vials within the cartridge 170.

Although not specifically shown in FIG. 4, the synthesizer 100 may have multiple sets of valves. The plurality of valves within the multiple sets of valves may be configured in a variety of ways to dispense the reagent solutions to a select one or more of the vials. For example, in one configuration, where each set of valves is identically configured, the synthesizer 100 is capable of simultaneously dispensing the same reagent solution in parallel from multiple sets of valves to corresponding banks of vials. In this configuration, the multiple banks of vials may be processed in parallel. In the alternative, each individual valve within multiple sets of valves may contain entirely different reagent solutions such that there is no duplication of reagent solutions among any individual valves in the multiple sets of valves. This configuration allows the synthesizer 100 to build polymer chains requiring a large variety of reagent solutions without changing the reagent solutions associated with each valve.

The motor 445 is preferably mounted to the base 105 through the gear box 440 and the motor connector 465. The chamber bowl 400 preferably surrounds the motor connector 465 and remains stationary relative to the base 105. The chamber bowl 400 is designed to hold any reagent solution spilled from the plurality of vials 160 during the purging process. Further, the chamber bowl 400 is configured with a tall shoulder to insure that spills are contained within the bowl 400. The chamber lip seal 450 preferably provides a seal around the motor connector 465 in order to prevent the contents of the chamber bowl 400 from flowing into the gear box 440. The chamber seal 450 is preferably composed of a flexible and resilient material such as Teflon® or elastomer which conforms to any irregularities of the motor connector 465. Alternatively, the chamber seal can be composed of any other appropriate material. Additionally, the chamber seal 450 has frictionless properties which allow the motor connector 465 to rotate freely within the seal. For example, coating this flexible material with Teflon® helps to achieve a low coefficient of friction.

The drain plate 410 is coupled to the motor connector 465. The cartridge 170 is coupled to the drain plate 410. More specifically, the drain plate 410 is attached to the motor connector 465 which rotates the drain plate 410 while the motor 445 is operating and the gear box 440 is turning. The cartridge 170 and the drain plate 410 are preferably configured to rotate as a single unit. The drain plate 410 is configured to catch and direct the reagent solutions as the reagent solutions are expelled from the plurality of vials. While operating, the motor 445 is configured to rotate both the cartridge 170 and the drain plate 410 through the gear box 440 and the motor connector 465. The chamber seal 450 allows the motor connector 465 to rotate the cartridge 170 and the drain plate 410 through a portion of the chamber bowl 400 while still containing any reagent solutions in the chamber bowl 400.

The controller 480 is coupled to the motor 445 to activate and deactivate the motor 445 in order to rotate the cartridge 170 and the drain plate 410. The controller 480 provides embedded control to the synthesizer and controls not only the operation of the motor 445, but also the operation of the valves 470 and the waste tube system 430.

Figure 5:
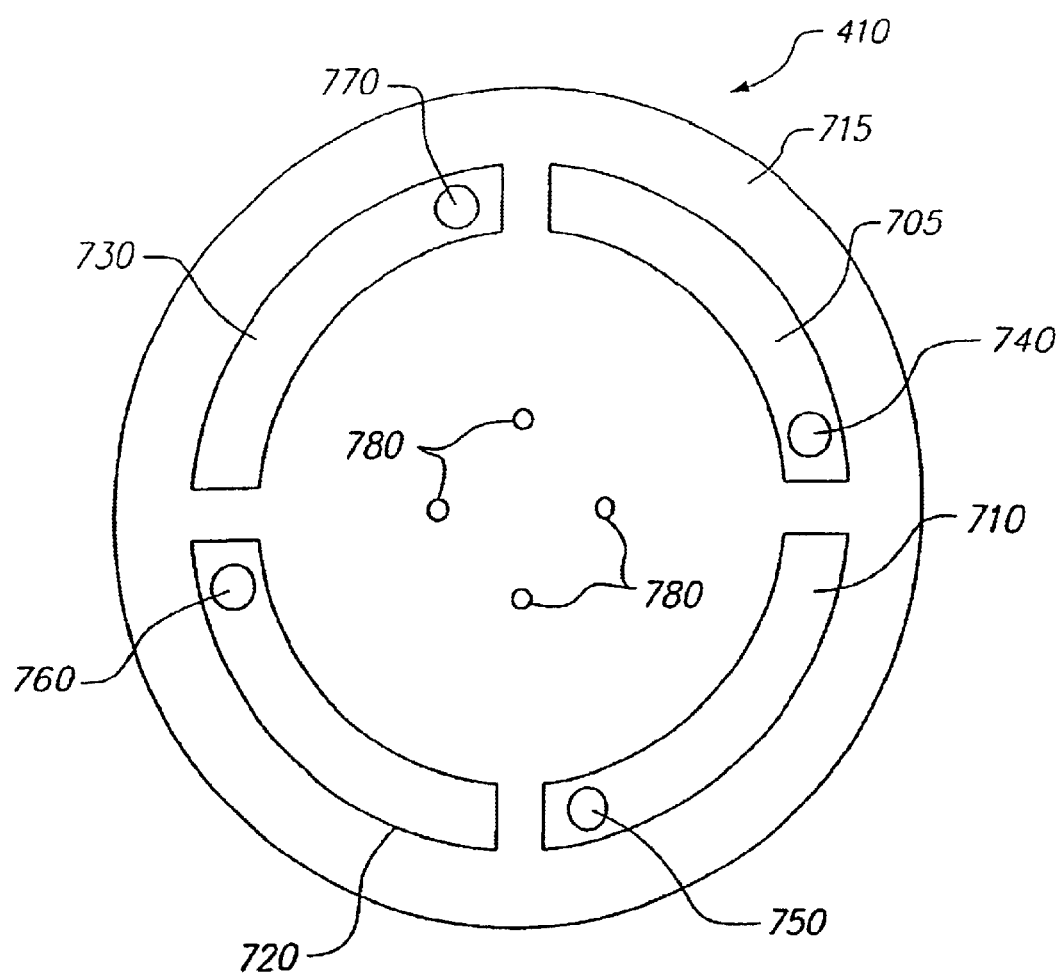
FIG. 5 illustrates a top view of the drain plate.

FIG. 5 illustrates a detailed top view of the drain plate 410. The drain plate 410 has a plurality of securing holes 780 for attaching to the motor connector 465. The drain plate 410 also has a top surface 715 which attaches to the underside of the cartridge 170. As stated previously, the cartridge 170 holds the plurality of vials grouped into the plurality of banks.

The drain plate 410 preferably has four collection areas 705, 710, 720 and 730, to correspond to the four banks within the cartridge 170. Each of these four collection areas 705, 710, 720 and 730 forms a recessed area below the top surface 715 and is designed to contain and direct material flushed from the vials within the bank above the collection area. Each of the four collection areas 705, 710, 720 and 730 is positioned below a corresponding one of the banks of vials on the cartridge 170. The drain plate 410 is rotated with the cartridge 170 to keep the corresponding collection area below the corresponding bank.

There are four drains 740, 750, 760 and 770, each of which is located within one of the four collection areas 705, 710, 720 and 730, respectively. In use, the collection areas 705, 710, 720 and 730 are configured to contain material flushed from corresponding vials and pass that material through the drains 740, 750, 760 and 770, respectively. Preferably, there is a collection area and a drain corresponding to each bank of vials within the cartridge 170. Alternatively, any appropriate number of collection areas and drains can be included within a drain plate.

The clear window 460 (FIG. 4) is attached to a top plate of the base 105 and covers the area above the cartridge 170. The top plate of the base 105 opens up allowing an operator or maintenance person access to the interior of the synthesizer 100. The clear window 460 allows the operator to observe the synthesizer 100 in operation while providing a pressure sealed environment within the interior of the synthesizer 100. As shown in FIG. 4, there are a plurality of through holes 520 in the clear window 460 to allow the plurality of dispense lines 140 to extend through the clear plate 460 to dispense material into the vials.

The clear window 460 also includes a gas fitting 530 attached therethrough. The gas fitting 530 is coupled to a gas line 540. The gas line 540 preferably continuously emits a stream of inert gas which flows into the synthesizer 100 through the gas fitting 530 and flushes out traces of air and water from the plurality of vials 160 within the synthesizer 100. Providing the inert gas flow through the gas fitting 530 into the synthesizer 100 prevents the polymer chains being formed within the vials from being contaminated without requiring the plurality of vials 160 to be hermetically sealed and isolated from the outside environment.

The drain 740 is attached to the drain plate 410 and is positioned to correspond with a bank of vials held within the cartridge 170. The drain 740 corresponds to a single bank of vials and is primarily utilized for flushing material from this single bank of vials. As described above, preferably, each bank of vials has a corresponding drain.

The waste tube system 430 is preferably utilized to provide a pressurized environment for flushing material including reagent solutions from the plurality of vials located within a corresponding bank of vials and expelling this material from the synthesizer 100. Alternatively, the waste tube system 430 can be used to provide a vacuum for drawing material from the plurality of vials located within a corresponding bank of vials.

Figure 7:
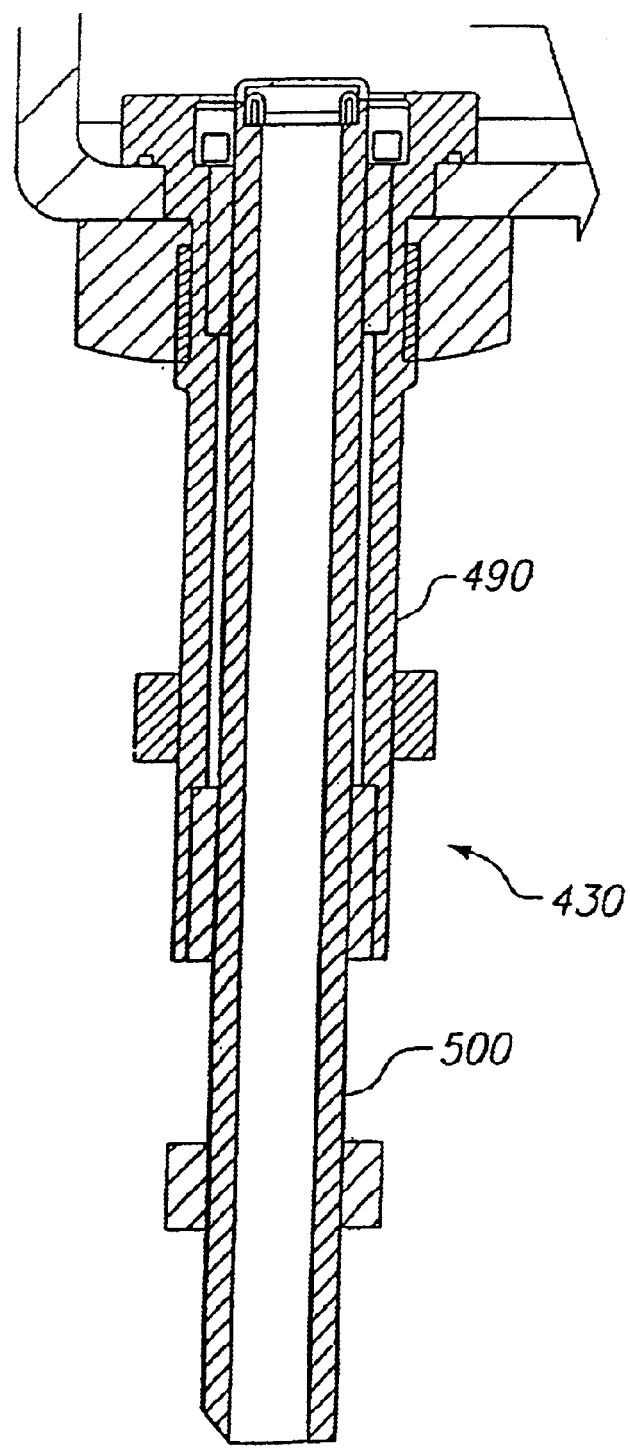
FIG. 7 illustrates a cross-sectional view of the waste tube system.

An isolated cross-sectional view of the waste tube system 430 is illustrated in FIG. 7. The waste tube system 430 comprises a stationary tube 490 and a mobile waste tube 500. The stationary tube 490 and the mobile waste tube 500 are slidably coupled together. The stationary tube 490 is attached to the chamber bowl 410 and does not move relative to the chamber bowl 400. In contrast, the mobile tube 500 is capable of sliding relative to the stationary tube 490 and the chamber bowl 400. When in an inactive state, the waste tube system 430 does not expel any reagent solutions. During the inactive state, both the stationary tube 490 and the mobile tube 500 are preferably mounted flush with the bottom portion of the chamber bowl 400.

When in an active state, the waste tube system 430 purges the material from the corresponding bank of vials. During the active state, the mobile tube 500 rises above the bottom portion of the chamber bowl 400 towards the drain plate 410. The drain plate 410 is rotated over to position a drain corresponding to the bank to be flushed, above the waste tube system 430. The mobile tube 500 then couples to this drain and the material is flushed out of the corresponding bank of vials and into the drain plate 420. The reagent solution is purged from the corresponding bank of vials due to a sufficient pressure differential between a top opening 610 (FIG. 6) and a bottom opening 640 (FIG. 6) of each vial. This sufficient pressure differential is preferably created by coupling the mobile waste tube 500 to the corresponding drain. Alternatively, the waste tube system 430 may also include a vacuum device 510 coupled to the stationary tube 490 wherein the vacuum device 510 is configured to provide this sufficient pressure differential to expel material from the corresponding bank of vials. When this sufficient pressure differential is generated, the excess material within the vials being flushed, then flows through the corresponding drain and is carried away via the waste tube system 430.

Figure 9:
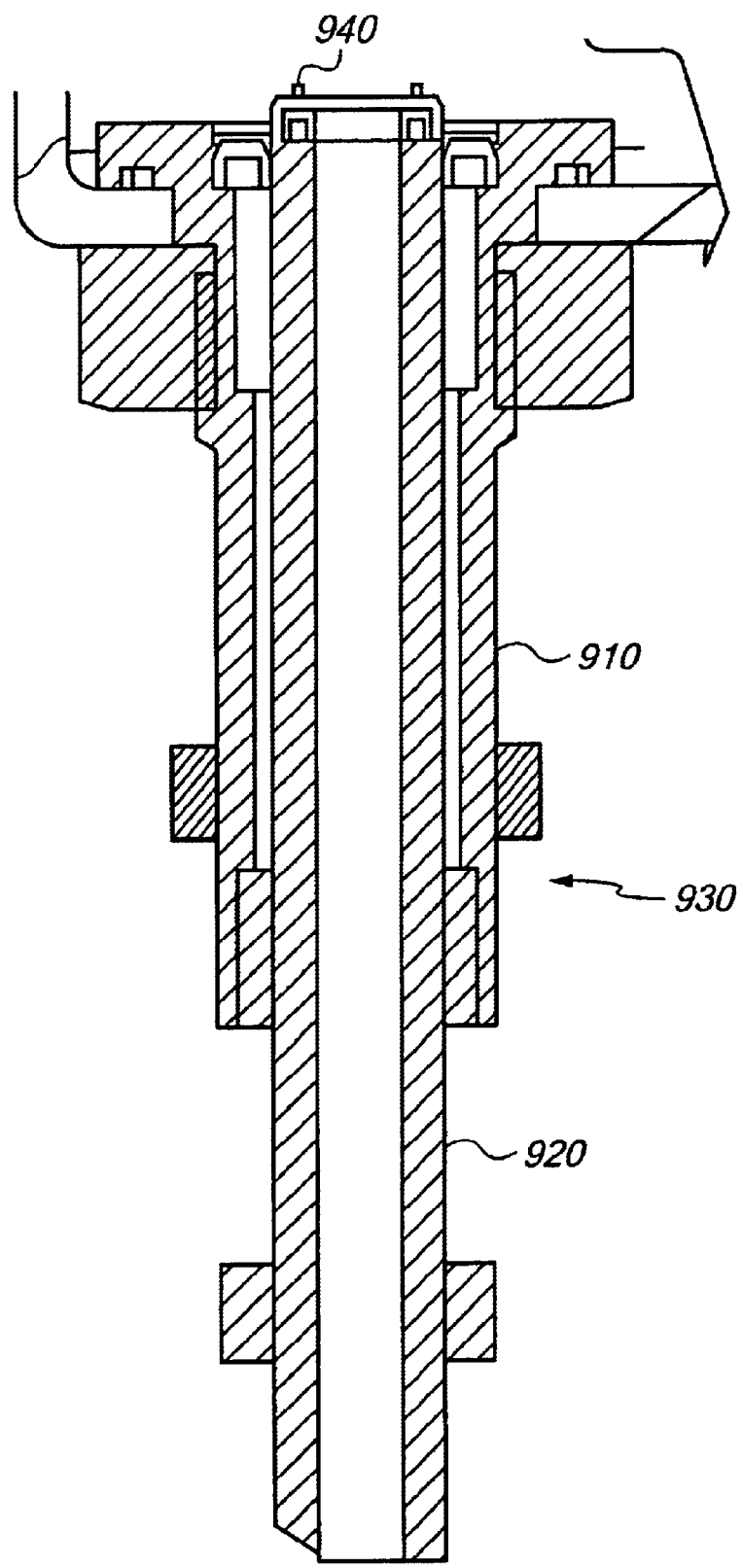
FIG. 9 illustrates a cross-sectional view of an alternate waste tube system.

When engaging the corresponding drain to flush a bank of vials, preferably the mobile tube 500 slides over the corresponding drain such that the mobile tube 500 and the drain act as a single unit. Alternatively, as illustrated in FIG. 9 the waste tube system 930 includes a mobile tube 920 which engages the corresponding drain by positioning itself directly below the drain and then sealing against the drain without sliding over the drain. The mobile tube 920 includes a drain seal 940 positioned on top of the mobile tube 920. In this embodiment, during a flushing operation, the mobile tube 920 is not locked to the corresponding drain. In the event that this drain is accidently rotated while the mobile waste tube 940 is engaged with the drain, the drain and mobile tube 920 of the synthesizer 100 will simply disengage and will not be damaged. If this occurs while material is being flushed from a bank of vials, any spillage from the drain is contained within the chamber bowl 400.

Configuring the waste tube system 430 to expel the reagent solution while the mobile waste tube 500 is coupled to the drain allows the present invention to selectively purge individual banks of vials. Instead of simultaneously purging all the vials within the synthesizer 100, the present invention selectively purges individual banks of vials such that only the vials within a selected bank or banks are purged.

Preferably, the synthesizer 100 includes two waste tube systems 430 for flushing two banks of vials simultaneously. Alternatively, any appropriate number of waste tube systems can be included within the synthesizer 100 for selectively flushing banks of vials.

Figure 6:
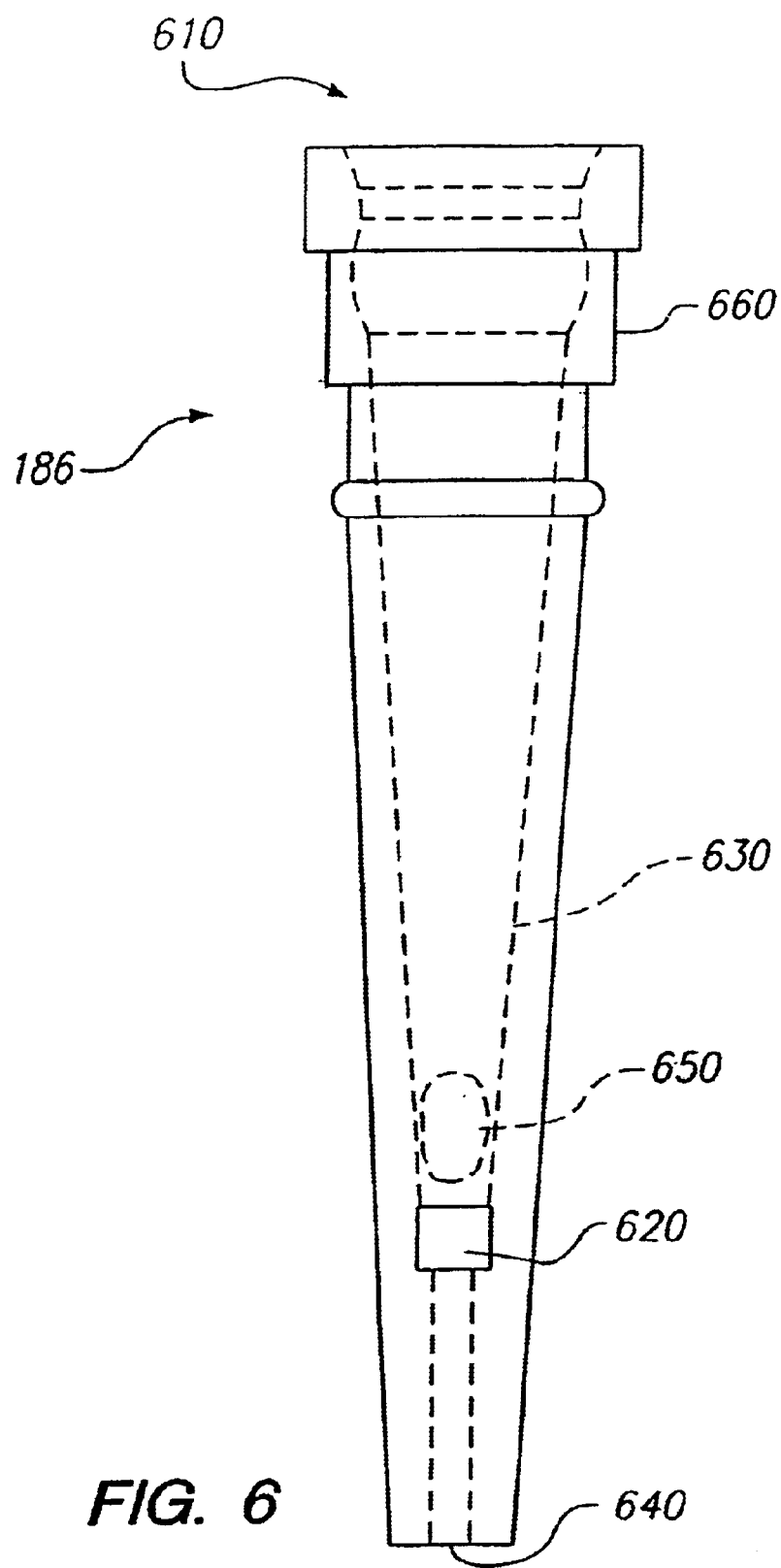
FIG. 6 illustrates a cross-sectional view of the vial.

FIG. 6 illustrates a cross sectional view of a vial 181. The vial 181 is an integral portion of the synthesizer 100. Generally, the polymer chain is formed within the vial 181. More specifically, the vial 181 holds a CPG 650 on which the polymer chain is grown. As stated previously, to create the polymer chain, the CPG 650 is sequentially submerged in various reagent solutions for a predetermined amount of time. With each deposit of a reagent solution, an additional unit is added to the resulting polymer chain. Preferably, the CPG 650 is held within the vial 181 by a frit 620. The vial 181 includes a top opening 610 and a bottom opening 640. During the dispensing process, the vial 181 is filled with a reagent solution through the top opening 610. Then, during the purging process, the vial 181 is drained of the reagent solution through the bottom opening 640. The frit 620 prevents the CPG 650 or other support from being flushed away during the purging process. A precision bored interior 630 holds the frit 620 in place and provides a consistent compression and seal with the frit 620. As a result of the precision bored interior 630, there is a consistent flow of the reagent solution through each vial during both the dispensing and purging processes.

The exterior of each vial 181 also has a precise dimension around the support 660. This support 660 fits within the receiving hole 185 within the cartridge 170 and provides a pressure tight seal around each vial within the cartridge 170. Preferably, each vial 181 is formed of polyethylene by a molded process. Alternatively, the vials 181 can be formed using any appropriate process and any appropriate material.

In use, the controller 480 which is coupled to the motor 445, the valves 470, and the waste tube system 430 coordinates the operation of the synthesizer 100. The controller 480 controls the motor 445 such that the cartridge is rotated to align the correct vials with the is dispense lines 140 corresponding to the appropriate valves 470 during dispensing operations and that the correct one of the drains 740, 750, 760 and 770, are aligned with an appropriate waste tube system 430 during a flushing operation.

Figure 8:
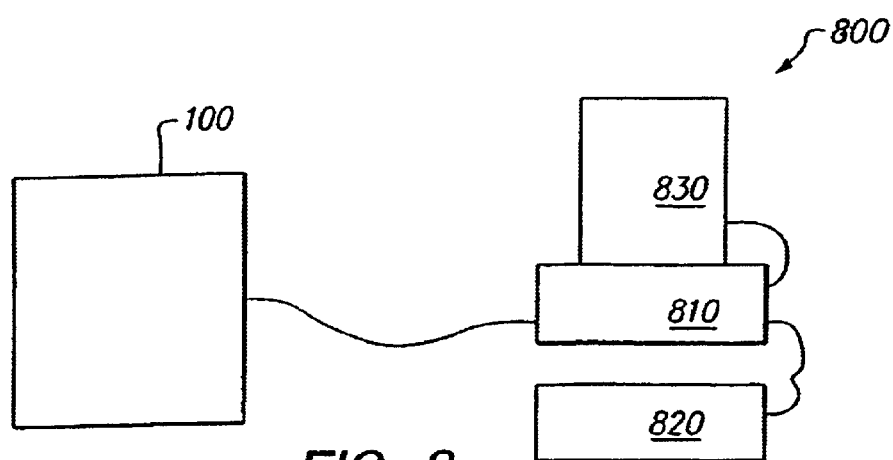
FIG. 8 illustrates the controlling computer coupled to the synthesizer of the preferred embodiment of the present invention.

FIG. 8 illustrates a computer system 800 coupled to the synthesizer 100. The computer system 800 preferably provides the synthesizer 100 and specifically the controller 480 with operating instructions. These operating instructions include rotating the cartridge 170 to a predetermined position, dispensing one of a plurality of reagent solutions into selected vials through the valves 470 and dispense lines 140, flushing the first bank of vials 115 and/or the second bank of vials 125, and coordinating a timing sequence of these synthesizer functions. Preferably, the computer system 800 allows the user to input data representing reagent solution sequences to form a polymer chain, oligonucleotides, and other organic compounds via a graphical user interface. After the user inputs this data, the computer system 800 instructs the synthesizer 100 to perform appropriate functions without any further input from the user. The computer system 800 preferably includes a processor 810, an input device 820 and a display 830. The computer 800 can be configured as a laptop or a desktop.

The present invention forms custom defined sequences such as oligonucleotides, polymers and other organic compounds. The present invention has a plurality of vials divided among a plurality of banks wherein a custom sequence can be synthesized within each vial. The present invention forms these custom sequences without constant supervision by the user.

Each bank of vials has a drain and can be selectively purged. To perform a purging operation, the drain of the corresponding bank of vials is coupled to a mobile waste tube. After coupling the drain to the mobile waste tube, a pressure differential is formed and the material within each of the vials within the corresponding bank of vials is expelled.

The present invention preferably utilizes a plurality of valves divided into a plurality of banks of valves to perform a filling operation to dispense reagent solutions to various vials during the filling operation. Each of the plurality of valves can be configured to dispense different reagent solutions to form complex custom sequences. In a parallel configuration, the plurality of valves can be configured to dispense the same reagent solution simultaneously to more than one vial.

The present invention allows the user to enter the custom sequence into a computer system. This computer system controls the fill operation and the purge operation such that appropriate vials are filled with the correct reagent solutions and the appropriate banks of vials are purged at the appropriate times within the sequence. Further, the computer system ensures that the correct quantity of reagent solution is deposited and that the reagent solution remains in the appropriate vial for the correct amount of time.

Each vial of the present invention has a precision bored interior that is configured to produce a consistent seal with a frit. By having the consistent seal with the frit, the reagent solutions flow evenly and predictably through each vial of the present invention. Each vial also includes a precise exterior dimension to consistently fit within the cartridge and provide a pressure tight seal around the vial within the cartridge.

In operation, when building sequence defined oligonucleotides, polymer chains or other organic compounds, the synthesizer 100 rotates the appropriate vials under the dispense tubes corresponding to the appropriate valves 470 at the appropriate times to build the desired sequence or compound. The synthesizer also rotates the banks of vials over a corresponding waste tube system 430 in order to flush material from the vials, as appropriate. As discussed above, the banks of vials held within a cartridge can be selectively purged to allow a user to potentially build different sequences or compounds within each vial. In this manner, one bank of vials can be purged, while another bank of vials is in a wait period. While purging one bank of vials, a dispense operation could also be performed on vials other than the bank or banks of vials being purged, if the position of the vials corresponds to the appropriate valves. However, during a purging operation, the cartridge 170 cannot be rotated or the drain 740 will disengage from the mobile waste tube 500.

To perform a dispense operation for a selected vial, the motor 445 rotates the cartridge 170 in response to the computer system 800 such that the vial 181 is positioned below the appropriate dispense line 140 corresponding to the valve 470. Once the vial 181 is properly positioned below this dispense line 140, the valve is opened by the controller 480 and the solution controlled by the valve 470 flows through the dispense tube 140 into the vial 181. The valve 470 is then closed after a predetermined period of time corresponding to the precise amount of solution to be dispensed into the vial 181.

To purge material from a bank of vials, the motor 445 rotates the cartridge 170 in response to the computer system 800 such that the drain corresponding to the bank of vials to be purged is positioned above the waste tube system 430. The mobile waste tube 500 is then raised to engage the drain and the material within the bank of vials is expelled from the vials through the waste tube system 430.

The present invention has been described in terms of specific embodiments incorporating details to facilitate the understanding of the principles of construction and operation of the invention. Such reference herein to specific embodiments and details thereof is not intended to limit the scope of the claims appended hereto.

It will be apparent to those skilled in the art that modifications may be made in the embodiment chosen for illustration without departing from the spirit and scope of the invention. Specifically, it will be apparent to one of ordinary skill in the art that the device of the present invention could be implemented in several different ways and the embodiments disclosed above are only exemplary of the preferred embodiment and the alternate embodiments of the invention and is in no way a limitation.

We claim:

1. A synthesizer for forming a polymer chain by sequentially adding monomer units found in one of a plurality of reagent solutions, the synthesizer comprising:

a. a first vial and a second vial, each for holding a selective one or more of the pluralityo f reagent solutions during synthesis;

b. means for dispensing configured for dispensing the selective one or more of plurality of reagent solutions into the first and second vials; and c. means for selectively expelling material from the first and second vials, configured for engaging a drain associated with a selective one of the first vial and the second vial and thereby purging material from a selective one of the first vial and the second vial when the drain is engaged.

2. The synthesizer according to claim 1 further comprising a cartridge configured for holding the first vial and the second vial.

3. The synthesizer according to claim 2 wherein the cartridge holds the first vial and the second vial along a circular perimeter of the cartridge.

4. The synthesizer according to claim 3 further comprising a motor coupled to the cartridge configured for selectively rotating the cartridge relative to the means for sequentially dispensing in a circular motion.

5. The synthesizer according to claim 4 further comprising a drain plate coupled to the cartridge for separating the first vial into a first bank of vials and the second vial into a second bank of vials.

6. The synthesizer according to claim 1 further comprising a chamber bowl coupled to the means for selectively expelling wherein the chamber bowl contains any spilled material.

7. The synthesizer according to claim 6 further comprising a seal coupled to the chamber bowl to prevent spilled material from escaping outside the chamber bowl.

8. The synthesizer according to claim 1 wherein the means for selectively expelling further comprises:

a. means for forming a pressure differential between a first opening and a second opening of the selective one of the first vial and the second vial; and b. a waste tube to collect material expelled from the selective one of the first vial and the second vial.

9. The synthesizer according to claim 1 wherein the means for dispensing further comprises:

a. a plurality of valves for controlling dispensing of the plurality of reagent solutions; and b. a plurality of dispense lines wherein each of the plurality of the dispense lines is coupled to a corresponding one of the plurality of valves for delivering one of the plurality of reagent solutions to a selected vial.

10. The synthesizer according to claim 1 wherein each of the first vial and the second vial further comprise a bored interior having a consistent dimension for maintaining a consistent flow through the first and second vials and are configured to hold a frit for retaining a solid material above the frit.

11. A synthesizer for forming a polymer chain by sequentially adding monomer units found in a plurality of reagent solutions, the synthesizer comprising:

a. a first vial for holding a selective one or more of the plurality of reagent solutions during synthesis;

b. a second vial for holding a selective one or more of the plurality of reagent solutions during synthesis;

c. a cartridge to hold the first vial and the second vial;

d. a dispensing system to dispense the selective one or more of the plurality of reagent solutions into the first and second vial; and e. a purging system to remove material from a selective one of the first vial and the second vial, wherein the purging system is configured to engage a drain associated with the selected one of the first vial and the second vial and purge material from the selected one of the first vial and the second vial when the drain is engaged.

12. The synthesizer according to claim 11 wherein the cartridge holds the first vial and the second vial along a circular perimeter of the cartridge.

13. The synthesizer according to claim 11 further comprising a chamber bowl coupled to the purging system wherein the chamber bowl contains spilled material.

14. The synthesizer according to claim 13 further comprising a seal coupled to the chamber bowl to prevent spilled material from escaping outside the chamber bowl.

15. The synthesizer according to claim 11 wherein the purging system further comprise:

a. means for forming a pressure differential between a first opening and a second opening of the selective one of the first vial and the second vial; and b. a waste tube to collect material expelled from the selective one of the first vial and the second vial.

16. The synthesizier according to claim 11 wherein the dispensing system further comprises:

a. a plurality of valves for controlling dispensing of the plurality of reagan solutions; and b. a plurality of dispense lines each coupled to one of the plurality of valves for delivering a corresponding one of the reagent solutions to a selected vial.

17. The synthesizier according to claim 11 wherein each of the first vial and the second vial further comprise a bored interior having a consistent dimension for maintaining a consistent flow through first and second vials and are configured to hold a frit for retaining a solid material above the frit.

18. The synthesizer according to claim 11 further comprising a drain plate coupled to the cartridge for separating the first vial into a first bank of vials and the second vial into a second bank of vials.

19. The synthesizer according to claim 11 further comprising a motor coupled to the cartridge to selectively rotate the cartridge relative to the dispensing system.

20. synthesizer for creating a polymer chain by sequentially adding monomer units found in one of a plurality of reagent solutions, the synthesizer comprising:

a. a plurality of vials each for holding material including a selective one of the plurality of reagent solutions during synthesis;

b. a cartridge for holding the plurality of vials and dividing the plurality of vials into a first bank of vials including at least one of the plurality of vials and a second bank of vials including at least one of the plurality of vials;

c. a first drain associated with the first bank of vials;

d. a second drain associated with the second bank of vials;

e. a dispensing system configured to sequentially dispense selective ones of the plurality of reagent solutions into the plurality of vials; and f. a purging system configured to purge material from a selective one of the first bank of vials and the second bank of vials, wherein the purging system is configured to engage the selected one of the first drain and the second drain to purge material.

21. The synthesizer according to claim 20 wherein the purging system further comprises waste tube capable of selectively coupling with a selective one of the first drain and the second drain to purge material from the first bank of vials and the second bank of vials.

22. The synthesizer according to claim 20 wherein the dispensing system further comprises:
  a. a plurality of valves for controlling the dispensing of the plurality of reagent solutions; and
  b. a plurality of dispense lines each coupled to one of the plurality of valves for delivering a corresponding one of the plurality of regent solutions to a selected vial.

23. A synthesizer for forming a polymer chain by sequentially adding monomer units found in one of a plurality of reagent solution, the synthesizer comprising:
  a. a cartridge configured to hold a first vial and a second vial, each for holding a selective one or more of the plurality of reagent solutions during synthesis;
  b. a dispensing system configured to dispense the selective one or more of the plurality of reagent solutions into the first and second vials; and
  c. a purging system configured to selectively expel material from the first and second vials, wherein a selective one or both of the purging system and the cartridge are moved in relation to each other in order to allow the purging system to engage a drain associated with a selective one of the first vial and the second vial and thereby expel material from to selected one of the first vial and the second vial through the purging system when the drain is engaged.

24. The synthesizer according to claim 23 wherein the cartridge holds the first vial and the second vial along a circular perimeter of the cartridge.

25. The synthesizer according to claim 23 further comprising a motor coupled to the cartridge configured to selectively rotate the cartridge relative to the dispensing system in a circular motion.

26. The synthesizer according to claim 23 wherein the dispensing system further comprises:
  a. a plurality of valves for controlling dispensing of the plurality of reagent solutions; and
  b. a plurality of dispense lines wherein each of the plurality of the dispense lines is coupled to a corresponding one of the plurality of valves for delivering one of the plurality of reagent solutions to a selected vial.

27. The synthesizer according to claim 23 wherein each of the first vial and the second vial further comprise a bored interior having a consistent dimension for maintaining a consistent flow through the first and second vials and are configured to hold a frit for retaining a solid material above the frit.

* * * * *

UNITED STATES PATENT AND TRADEMARK OFFICE
CERTIFICATE OF CORRECTION

PATENT NO. : 6,811,755 B2
DATED : November 2, 2004
INVENTOR(S) : Gary R. McLuen et al.

It is certified that error appears in the above-identified patent and that said Letters Patent is hereby corrected as shown below:

Column 8,
Line 31, delete "940" and insert -- 920 --.

Column 11,
Line 2, delete " pluralityo f" and insert -- plurality of --.
Line 5, insert -- the -- after "selective one or more of".
Line 67, delete "vial"and insert -- vials --.

Column 12,
Line 18, delete "comprise" and insert -- comprises --.
Line 28, delete "reagan"and insert -- reagent --.
Line 44, insert -- A -- before "synthersizer".
Line 67, insert -- a -- before "waste tube"

Column 13,
Line 10, delete "regent" and insert -- reagent --.
Line 13, delete "solution" and insert -- solutions --
Line 27, delete "to" and insert -- the --.

Signed and Sealed this

Thirty-first Day of May, 2005

JON W. DUDAS
*Director of the United States Patent and Trademark Office*